United States Patent [19]
Kendrick

[11] Patent Number: 4,708,131
[45] Date of Patent: Nov. 24, 1987

[54] COLLAPSIBLE FEMUR TRACTION DEVICE

[76] Inventor: Richard L. Kendrick, 1573 Kimberly Woods, El Cajon, Calif. 92020

[21] Appl. No.: 899,729

[22] Filed: Aug. 25, 1986

[51] Int. Cl.$^4$ .............................................. A61F 5/04
[52] U.S. Cl. .................................. 128/85; 128/84 R; 128/87 R; 128/75
[58] Field of Search ..................... 128/83, 84 R, 84 C, 128/85, 87 R, 88, 89 R, 75, 80 R; 135/7, 4, 75, 105

[56] References Cited

U.S. PATENT DOCUMENTS

| | | | |
|---|---|---|---|
| 2,198,908 | 4/1940 | Ellis | 128/84 R |
| 3,669,133 | 6/1972 | Hyman | 135/74 |
| 4,236,543 | 12/1980 | Moss | 135/106 X |
| 4,328,794 | 5/1982 | Holmes | 128/85 |

Primary Examiner—Robert A. Hafer
Assistant Examiner—Kathleen J. D'Arrigo
Attorney, Agent, or Firm—Ralph S. Branscomb

[57] ABSTRACT

A collapsible femur traction device utilizes a segmented pole with an internal elastic cord running through the segments which will hold any desired number of the segments together to establish different effective lengths of the pole, so that the traction device can be used on small children as well as large adults, and is also collapsible into a very compact form. At the upper end of the pole, the segments are pulled apart and bent over double to achieve the proper length, with the adjacent ends of the pole inserted into a double socket which is attached to a strap on the upper thigh of the broken leg. A tensionable harness around the ankle applied traction to the leg by pulling it toward the opposite end of the pole, which extends beyond the foot.

8 Claims, 11 Drawing Figures

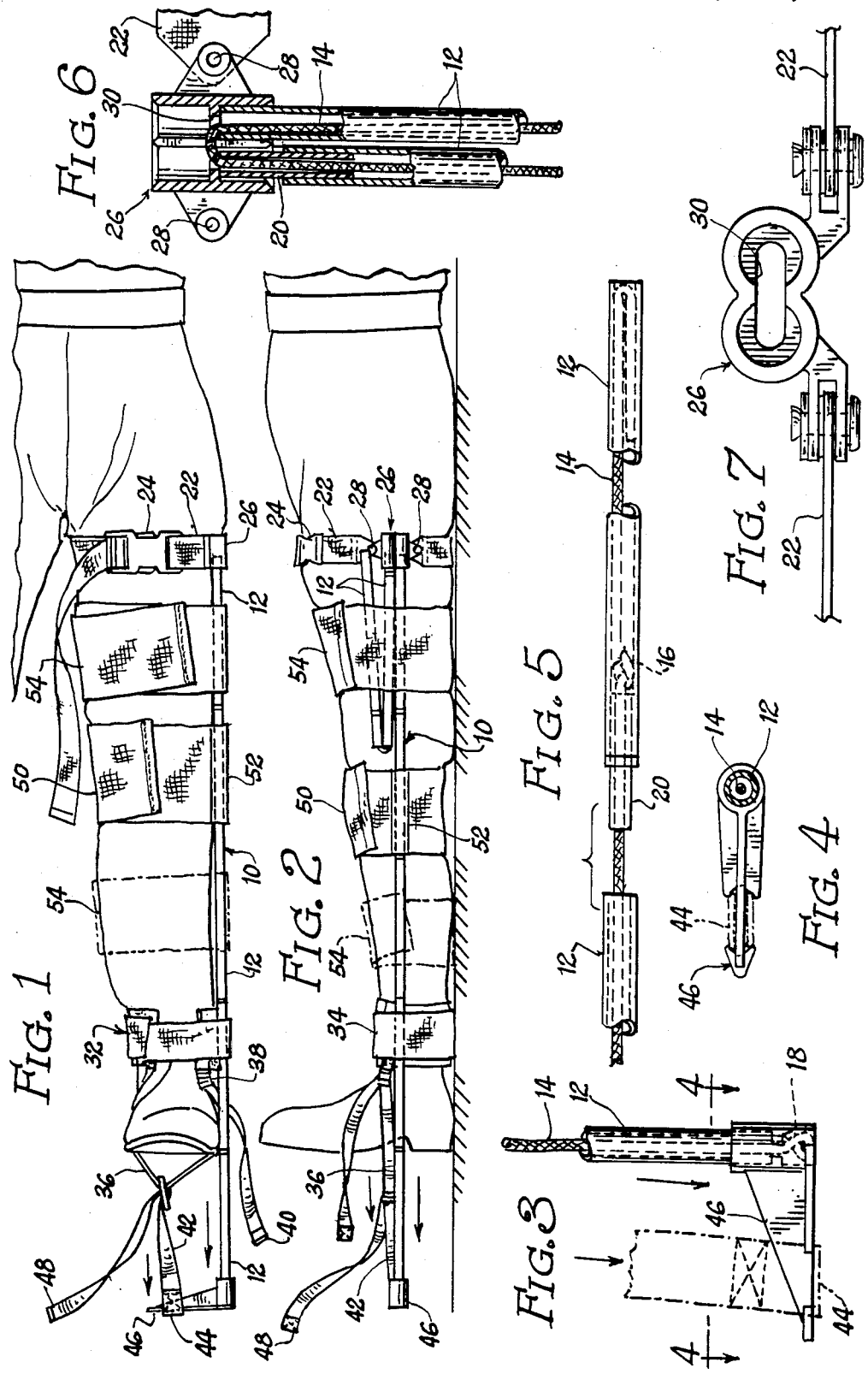

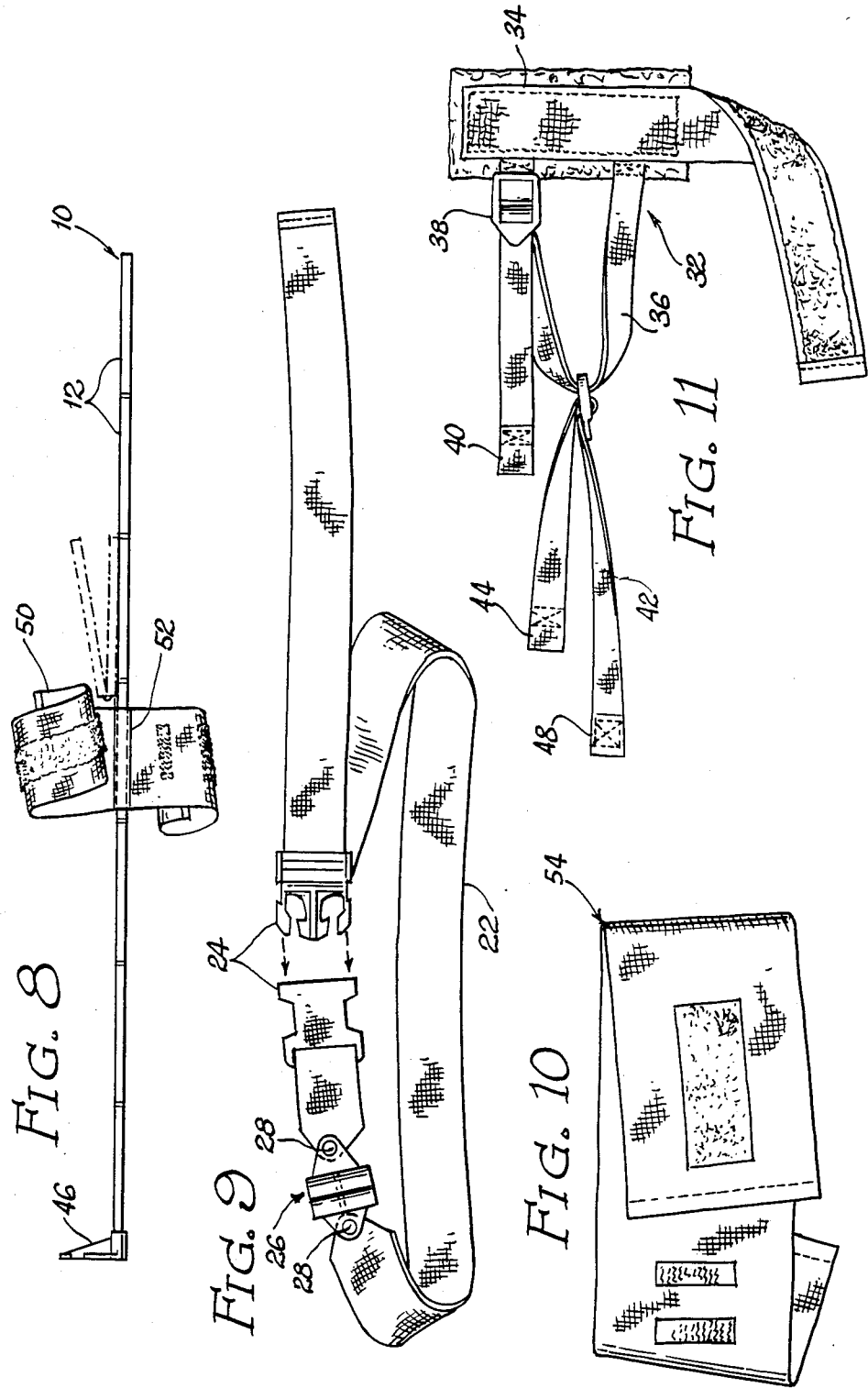

COLLAPSIBLE FEMUR TRACTION DEVICE

BACKGROUND OF THE INVENTION

The invention is in the field of paramedical assistance devices and the provision of emergency aid to a victim suffering from a broken femur.

When the femur is broken, the muscles will involuntarily contract unless traction is applied to the leg. If the muscles are left to contract involuntarily for a period of time, they will begin undergoing spasms, and then often will go into fibrulation, in which they are spastically vibrating totally beyond the control of the victim. Especially in the case of a complex fracture when the broken segments of the femur are misaligned, with the jagged broken portions digging into the flesh, spasms or fibulation can be an extremely serious threat to the well-being and life of the victim. Large arteries and other blood vessels passing alongside the femur bone are at risk of being severed, which could cause rapid loss of blood and death in two to three minutes and the conseqential death of the patient.

For this reason, when a paramedic is at the scene of an accident and the accident victim has a broken femur, the leg is put in traction right away with a portable traction device before the victim is taken to the hospital.

There is one prior art traction device on the market which is widely used by paramedic units. This device has several areas in which improvements could be made, and to which the instant invention is addressed. That unit utilizes two poles or braces, extending along opposite sides of the leg. Because if is not lengthwise adjustable, two sizes must be carried in the paramedic unit—one pediatric version and one for adults. The brace extends below the foot, and to put a small child in an adult's brace would result in the awkward protrusion of the brace well below the foot, as much as two or three feet, creating an inconvenience and an unacceptable risk of further injury because of the awkwardness of the arrangement.

Another disadvantage of the prior art traction device lies in its high cost. Paramedics will often carry emergency equipment in the trunks of their private vehicle, but the cost of the unit on the market makes this prohibitive. Also, the prior art device is not lengthwise collapsible, it is somewhat time-consuming to use, and is relatively heavy.

Another problem with the prior art device relates to its efficacy as an aid in protection of the well-being of the victim. The prior art device has a cross bar that passes beneath the thigh from the outer brace to the inner brace, connecting them together. This does not present a problem when the patient is lying prostrate, beyond perhaps the slight discomfort of the feel of the bar passing under thigh just below the buttock. However, if other injuries have interfered with the victim's breathing, the standard procedure is to tilt up his torso, which frees his breathing somewhat. When this is done and the femur is in traction with the prior art device, the thigh is pressed against the cross bar with considerable pressure, causing the crossbar to dig into the flesh of the victim, which may severely pinch the sciatic nerve which runs along the bottom of the thigh, possibly causing further injury to the victim.

SUMMARY OF THE INSTANT INVENTION

The instant invention is addressed toward the above-stated drawbacks in the prior art and consists of a lightweight, aluminum segmented pole with an internal bunge cord which extends the length of the pole and will line up and hold as many of the segments together as desired, with the remaining, unused segments being folded down alongside the used portion, inside cloth sleeves that wrap around the leg. A special double-barreled socket is swivel-mounted to the thigh strap, and the doubled-over portion of the segmented pole is inserted into the socket after the appropriate length has been selected.

An ankle harness at the bottom end of the pole is quickly engaged around the ankle, with a tensioning strap engaging the tip of the pole, and a quick tug on a pair of straps which are part of the ankle harness will instantly tension the leg. Several cuffs are provided with Velcro TM fasteners to wrap around the leg to hold it to the pole.

This construction is much cheaper than models currently on the market by a factor of at least three, and in some cases more. Additionally, whereas it takes two technicians three to five minutes to use existing units, the tensioner disclosed and claimed herein can be deployed and used by one person in less than a minute. It is also much lighter than current units, and can be folded up into a space about 4" wide, and only 9½" long, compared to the 3' to 4' in length of the most widely used existing unit. It weighs less than 20 oz. compared to the 5 lbs. to 8 lbs. of the currently used portable traction devices.

BRIEF DESCRIPTION OF THE DRAWINGS

FIG. 1 is a top plan view illustrating the traction device in use on a broken leg;

FIG. 2 is a side elevation view of the leg in traction as shown in FIG. 1;

FIG. 3 is a detail illustrating the end of the traction pole;

FIG. 4 is a section taken along line 4—4 of FIG. 3;

FIG. 5 is a detail view of the segmented pole illustrating how the segments come apart when the elastic cord is stretched;

FIG. 6 is a section taken through the socket that holds the segmented pole to the thigh strap;

FIG. 7 is a top plan view of the socket;

FIG. 8 illustrates the segmented pole with the knee sleeve in place and with two segments bent over in phantom;

FIG. 9 illustrates the thigh strap;

FIG. 10 illustrates the ankle cuff; and,

FIG. 11 illustrates the ankle harness structure separated from the rest of the device.

DETAILED DESCRIPTION OF THE PREFERRED EMBODIMENT

The segmented pole 10 which is at the heart of the invention is best shown in FIGS. 3, 5, and 8. As can be seen in FIGS. 3 and 5, the segments 12 are held together by an elastic cord 14 that is knotted at the ends as indicated at 16 in FIGS. 5 and 18 in FIG. 3. As shown in FIG. 5, the end of the cord is doubled over so that it can be removed if necessary for replacement. Each of the segments has a reduced end 20 that permits it to telescope inside the end of the next segment. With the internal elastic cord, the action of assembling the segments together is very smooth, with the segments almost seating themselves with little additional manual effort.

In the preferred embodiment of the invention and in the production model, the segments are eight inches long and seven in number, so the overall length of the pole is close to five feet. That much length would only be needed for a very tall person, taller than the 6' 2" to 6' 4" range beneath which six segments will be adequate. Therefore, ordinarily one or more of the segments would not be used. Although it would be possible to use the entire length for people of ordinary height, this would result in an ordinate length of unnecessary pole extending below the foot, which only hinders the efforts of the paramedics.

To shorten the pole, as shown in FIG. 8, at any joint the segments are merely pulled apart, which can be done with a fairly light finger touch, with the unused segments being doubled back on the rest of the pole.

The first, or top, end of the pole is engaged by the thigh strap 22, which wraps around the upper thigh and has a quick-release, quick-tightening buckle 24. The thigh strap mounts a double-barreled socket 26, which is connected at both sides by swivels 28 so that it has the proper angular adjustability in use. The double socket engages the bent-over pole segments as indicated in FIG. 2, there being a cutaway portion 30, shown in FIGS. 6 and 7, to accommodate the elastic cord at the bend. The socket is symmetrical, so that either side could be used. This is a very useful feature, because in the field, when such emergency devices are generally being used, it is typically dark, the weather may be bad, and confusion rules. By making the socket double-ended, it makes no difference whether the operator gets it on right side up or upside down.

The pole is designed to extend a few inches below the bottom of the foot as shown in FIGS. 1 and 2. To engage the foot, there is an ankle harness structure 32 that has a padded cuff 34 and Velcro TM fastener material. When the cuff is wrapped around the ankle, a stirrup strap 36 passes over the foot as shown in FIGS. 1 and 2, and the adjustable buckle 38 permits the stirrup strap to be tightened down by pulling the end 40 once the cuff is on the ankle. A tensioning strap 42 has a small loop 44 in one end which slips over the small arm 46 at the lower end of the pole. The arm is shaped as shown in FIG. 4 so that once the loop is slipped over it, it will remain in place securely.

Once the tensioning strap is in place, the end 48 is pulled, tightening the entire ankle harness and tensioning the leg. Again, because of the conditions that usually prevail at accident sites, it is highly desirable that the straps be color coded to assist the operator in correctly sequencing the steps of attachment. First, the ankle strap is put in place, and then ideally the tightening end 40 of the stirrup strap would be color coded green; the plastic arm 46, yellow; and the tip of the tensioning strap 48, red, so that the green-yellow-red sequence would be easy to remember and guide the operator under stress conditions so that the attachment would go smoothly.

In order to maintain the leg straight, there is a central sleeve 50 into which is sewn a small sleeve 52 which slides frictionally along the pole. This sleeve is ordinarily used in the knee region. Other separate sleves are indicated at 54 are not attached to the pole as such, but are wrapped around the pole and leg after the pole is in place.

As discussed in the background, it is desirable not to have rigid structure passing under the thigh because of the possibility of pinching the sciatic nerve when the torso is elevated to facilitate breathing. The structure of the present invention accomodates this need. The pole which tensions the leg extends solely along the outside of the leg, and the only structures passing beneath the leg are flexible straps. With the flexible straps, there is essentially no more pressure on the sciatic nerve when the torso is inclined than there when the patient is prostrate. In the specific situation in which the victim has not only a broken femur but also constricted breathing, this is a serious and major advantage.

When the unit is not in use, all of the pole segments are collapsed and the entire structure fits in a very small bag, about 4" in diameter and 9" long. Because of its small size, and weighing just over 1 lb., it is very advantageous for use in the relatively cramped space of a paramedic vehicle, and even more so in mountain and wilderness rescue situations.

With these advantages, in addition to the major advantage of being much faster to use than existing units, and costing only a fraction as much, the unit is a real contribution to emergency and paramedical equipment.

I claim:

1. A collapsible femur traction device for use applying traction to a leg with a broken femur, comprising:
   (a) a thigh strap adapted to engage around the leg at the upper thigh;
   (b) a hollow pole made of segments connected with an internal elastic cord and capable of being used with selected numbers of segments to achieve selected length, and means on said thigh strap said means engaging either one of said pole or the ends of two pole segments connected by said elastic cord, depending on the length selected, with a second end of said pole adapted to extend down along the leg beyond the foot;
   (c) a tensioning harness adapted to engage around the ankle and having means engaging the second end of said pole and tension the leg by pulling the foot and the second end of the pole together.

2. Structure according to claim 1 wherein said tensioning harness is adapted to engage around the ankle has an ankle cuff, an adjustable stirrup strap mounted to said cuff adapted for looping around the foot, and a tensioning strap connected to the second end of said pole and joined to said stirrup strap with a tensioning buckle,
   said stirrup strap having a color-coded end which is used to adjust it, one end of said tensioning strap being color-coded, and the tip end of said pole to which the tensioning strap attaches being color-coded, to assist the operator in properly sequencing the attachment of the ankle harness.

3. Structure according to claim 1 wherein the second end of said pole defines a substantially orthogonal, cantilevered projecting arm, and said means to engage the second end of said pole comprises a loop defined in said tensioning harness engageable over the end of said arm.

4. Structure according to claim 1 wherein said thigh strap and tensioning harness are capable of engaging said pole such that same is adapted to extend along the outside of the leg, and including a plurality of releasable flexible sleeves fastenable around the leg and the pole to maintain same together, such that no rigid structure whatsoever is defined by the traction device which underlies the broken leg or is longer than the longest one of said segments.

5. Structure according to claim 4 wherein said segments are on the order of six in number and are of substantially the same length.

6. A collapsible femur traction device for use applying traction to a leg with a broken femur, comprising:
(a) a thigh strap adapted to engage around the leg at the upper thigh;
(b) a pole made of segments and capable of being used with selected numbers of segments to achieve a selected length, and means on said thigh strap to engage one end of said pole with a second end of said pole adapted to extend down along the leg beyond the foot;
(c) a tensioning harness adapted to engage around the ankle and having means to engage the second end of said pole and tension the leg by pulling the foot and the second end of the pole together;
(d) said pole being hollow, and having an internal elastic cord tensioning the segments together; and,
(e) said means on said thigh strap to engage one end of said pole comprising a double socket to accommodate the adjoining ends of a pair of adjacent pole segments which are separated and doubled over.

7. Structure according to claim 3 wherein said double socket is also double-ended and either end can accommodate the ends of a pair of doubled-over segments.

8. Structure according to claim 3 wherein said double socket is swivel-mounted at both sides to said thigh strap.

* * * * *